United States Patent [19]

Schulman

[11] 3,942,535
[45] Mar. 9, 1976

[54] RECHARGEABLE TISSUE STIMULATING SYSTEM

[75] Inventor: Joseph H. Schulman, Los Angeles, Calif.

[73] Assignee: G. D. Searle & Co., Skokie, Ill.

[22] Filed: July 26, 1974

[21] Appl. No.: 491,974

Related U.S. Application Data

[63] Continuation of Ser. No. 401,406, Sept. 27, 1973, abandoned.

[52] U.S. Cl. ......................................... 128/419 PS
[51] Int. Cl.² ........................................... A61N 1/36
[58] Field of Search ........ 128/2.05 S, 2.06 E, 2.1 A, 128/418, 419 C, 419 EP, 419 PG, 419 PS, 419 R, 420, 421, 422, 423, 419 PT; 307/91; 320/31, 32, 37, 39; 328/84; 336/84

[56] References Cited
UNITED STATES PATENTS

| | | | |
|---|---|---|---|
| 3,195,540 | 7/1965 | Waller | 128/419 PG |
| 3,409,007 | 11/1968 | Fuller | 128/2.06 E |
| 3,426,748 | 2/1969 | Bowers | 128/419 PS |
| 3,454,012 | 7/1969 | Raddi | 128/419 PG |
| 3,612,041 | 10/1971 | Ragsdale | 128/2.06 A |

FOREIGN PATENTS OR APPLICATIONS

| | | | |
|---|---|---|---|
| 87,174 | 5/1966 | France | 128/419 PS |

OTHER PUBLICATIONS

Evalenko et al., "Medical Instrumentation," Mar.-Apr., 1967, pp. 13–16.

Primary Examiner—William E. Kamm
Attorney, Agent, or Firm—Walter C. Ramm; Charles H. Thomas, Jr.; Peter J. Sgarbossa

[57] ABSTRACT

A rechargeable tissue stimulating system with a telemetry controlled power source. A constant current power source acting through an induction coil externally located with respect to a living patient is used to induce current flow in a charging circuit located beneath the skin of the patient. The charging circuit, in turn, recharges a battery which powers an electronic generator used for applying electrical pulses to stimulate living tissue in order to maintain bodily functions in the patient. A telemetry circuit connected to the charging circuit provides a magnetic output signal controlling externally located means associated with the power source. Such external means in response to this signal modulate the strength of the charging magnetic field, as well as provide visual or audio indication of proper charging as well as the proper positioning of the external power source with respect to the implanted charging circuit, completion of the proper charging interval to restore the amount of current used, and improper charging.

11 Claims, 12 Drawing Figures

TISSUE STIMULATOR

RECHARGEABLE TISSUE STIMULATING SYSTEM

This is a continuation, of application Ser. No. 401,406, filed Sept. 27, 1973 and now abandoned.

This invention relates to a rechargeable tissue stimulating system for providing a charge to a voltage source implanted in a living being, and for regulating recharging of the voltage source through the use of a telemetry circuit.

Tissue stimulating systems currently find a principal application in maintaining heart rhythm in a living patient through an implanted electrical pulse generating source. While such devices are used almost exclusively as cardiac pacers, they may also find other applications, including the actuation of prosthetic devices, and correction for respiratory and circulatory disfunctions.

When utilized for the purpose of maintaining an acceptable heartbeat in a patient, a catheter is passed through a vein and wedged into the heart muscle at the bottom of the right ventricle. The catheter leads to a pulse generator operated by a d.c. voltage source and located externally of the rib cage beneath the surface of the skin of the patient. To avoid the physical dangers and psychological distaste for frequent periodic operations to replace the voltage source, it has been found highly desirable to utilize a cardiac pacer employing a rechargeable voltage source. A very suitable voltage source has been found to be a single cell nickel-cadmium battery capable of producing a nominal 1.25 volts with a capacity of 200 milliamp hours. Such a voltage source will have a useful life of approximately 10 years. Other conventional voltage sources for pacemakers have a much shorter useful life averaging approximately 22 months.

With a rechargeable voltage source and with a reduction in the physical size of cardiac pacers, it has become very difficult to accurately locate the charging circuit for the pacer and to insure that recharging actually does occur when the power source for recharging the battery is in operation. It is particularly significant in this regard that recharging is a brief but frequent task which is desirably performed by the patient at his convenience. Since charging usually does not occur in the presence of a physician, the physician is unable to positively determine that proper periodic charging has occurred due to physiological changes in the patient, such as increased pulse rate. Indeed, even if recharging were to take place in the presence of a physician, the physician would not be able to ascertain with any degree of certainty whether or not the rechargeable battery actually received the appropriate charge.

Accordingly, it is an object of the present invention to substitute a telemetered signal indicative of proper charging of the implanted voltage source for the subjective observations of either the patient or his physician. In this manner, insufficient recharging or a total failure to recharge is detected by the charging circuitry itself, and a signal is returned to the recharging power source to indicate the charging status of the tissue stimulating system. This signal governs the operation of the recharging unit by extending the charging interval to compensate for periods during which improper charging occurs, and by indicating the termination of the charging interval as well as the failure of the unit to properly recharge.

It is a further object of the present invention, utilizing preferred embodiments thereof, to provide and automatically maintain a record of charging and discharging of the tissue stimulating system. In this way a physician avoids having to rely on the memory of his patient to determine the extent to which a charge exists in the rechargeable voltage source in the pacer.

A further object is to employ a system facilitating the proper positioning of the external charging head containing the power source induction coils with respect to the implanted charging circuit. This insures that proper positioning of the charging head is initially achieved, since a positive signal is generated persuant to this invention to notify the patient once proper positioning has been achieved. In addition, utilizing the special vest of this invention, proper positioning, once achieved, is automatically maintained for the duration of the charging interval.

It is a further object, utilizing the improved circuitry of this invention, to provide electrical shunt regulation in the charging circuit in order to prevent the voltage and current applied to the rechargeable voltage source from becoming too great. The circuitry of this invention also prevents the rechargeable voltage source from being drained of power if a short were to occur in the charging circuit.

In a broad aspect this invention is a rechargeable tissue stimulating system comprising: an implantable electrical tissue stimulator including a rechargeable d.c. voltage source for powering an electronic generator used for applying electrical pulses to stimulate living tissue in order to maintain bodily functions of a living subject into which it is implanted; an implantable charging circuit positioned beneath the skin of a living subject and including an induction coil with rectified output leads connected to said tissue stimulator; an external electrical charging power source including an induction coil for positioning external to a living subject and proximate to the induction coil of the implantable charging circuit; a telemetry circuit connected to said implantable charging circuit for detecting the magnitude of a charging current received by said d.c. voltage source and providing a magnetic output signal to said external power source indicative of the magnitude of the charging current received by said d.c. voltage source; and, a transducer forming a part of said external power source for converting said magnetic output signal to an electrical control signal, and wherein said external charging power source additionally includes a voltage control actuated by said control signal to adjust the strength of the magnetic field applied to said implantable charging circuit.

In a more specific application, this invention may be considered as a rechargeable cardiac pacing system for maintaining a source of stimulating pulses to the heart of a patient comprising in combination: an implantable cardiac stimulator for positioning beneath the skin of a patient equipped with a rechargeable d.c. voltage source, a pluse generating circuit, and catheter means equipped with electrodes for applying stimulating pulses to the heart of the patient; an implantable charging circuit for positioning beneath the skin of a patient and including an induction coil with rectified output leads connected to said d.c. voltage source; an external electrical charging power source including an induction coil for external positioning with respect to the patient proximate to the induction coil of the implantable charging circuit; a telemetry circuit connected to said implantable charging circuit for detecting the magnitude of a charging current received by said d.c. voltage source, and providing a magnetic output signal indicative thereof, and timing means responsive to said magnetic output signal including a register for storing a signal indicative of time elapsed during which the magnetic output signal indicates that the charging current is at least as great as a predetermined minimum operating level. In a more precise application, the magnetic output signal can be used to indicate the time elapsed during which the charging current is maintained within preset upper and lower limits.

This invention may be described with greater particularity by reference to the accompanying drawings in which:

FIG. 1 is a block diagram of the tissue stimulating system,

FIG. 2 is a schematic electrical diagram of the charging and telemetry circuit of FIG. 1, FIG. 3 is an electrical schematic diagram of a tissue stimulator according to FIG. 1, FIG. 4 is an electrical schematic diagram of the charge head and power source circuits of FIG. 1, FIG. 4A is an electrical schematic diagram of a portion of the transducer of FIG. 1, FIG. 4B is an electrical schematic diagram of the remaining portion of the transducer of FIG. 1, FIG. 5 is an electrical diagram illustrating various additional features of the tissue stimulating system of FIG. 1, FIG. 6 is a front perspective view of a portable power source and transducer.

Figure 1:
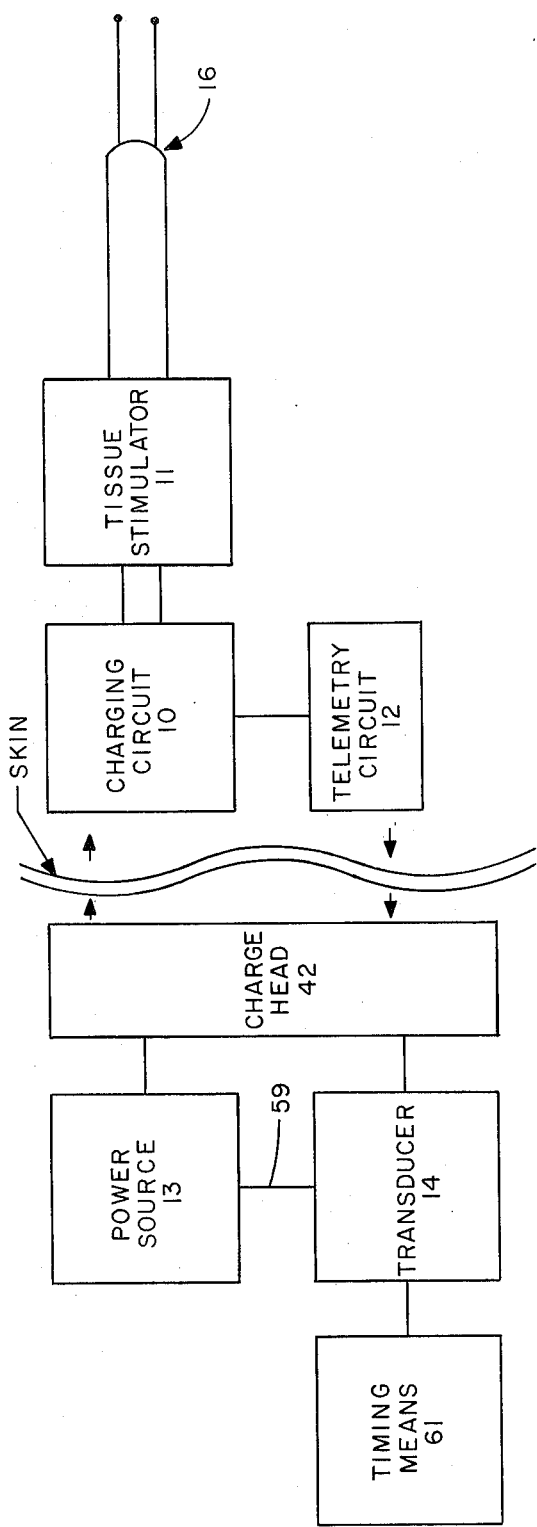

Referring now to FIG. 1, there is illustrated a rechargeable tissue stimulating system comprising a charging circuit 10 including a telemetry circuit 12 and a tissue stimulator 11 including a catheter 16, all designed for implantation into the body of a living patient. The system further includes a power source 13 with a transducer 14 in the form of a detector circuit for recharging and for verifying the charging condition of the implanted portions of the tissue stimulating system. The power source 13 employs a power oscillator circuit 104 to generate a 21 kilohertz electric field which powers the charge head 42. Part of this field is detected on the charging head 42 and sent to the detector circuit, or transducer 14. The output of transducer 14 is used to control the power oscillator output energy and is used to drive the timing means 61, which includes a timing and indicator circuit.

Figure 2:
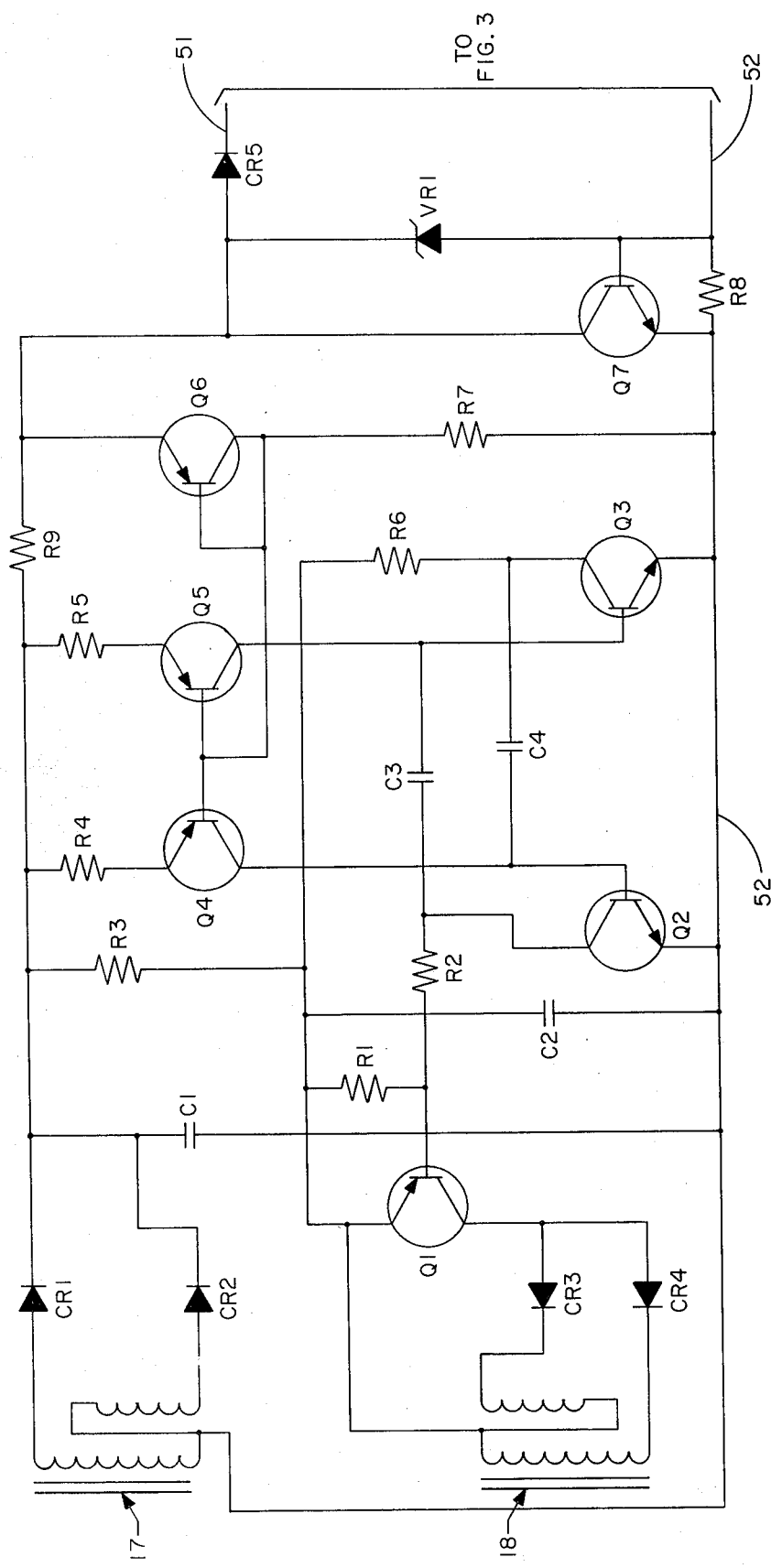

The charging circuit is illustrated in FIG. 2 and includes two induction coils 17 and 18. The output leads 51 and 52 from the induction coil 17 are rectified and are connected to the tissue stimulator of FIG. 3. The induction coils 17 and 18 are broad band frequency coils, not tuned coils. This is advantageous in that the system does not have to be critically tuned and may be recharged at a different frequency if that is found desirable (e.g. to avoid a specific interference with external nearby electrical equipment). A 21 kilohertz charging signal is generated by the power source 13 for recharging the battery 15 of the tissue stimulating system. This frequency is preferred because it is a low frequency that is also above audio; however, any frequency which will permit energy passage through tissue without excessive loss may be used. The entire waveform of the current induced in the induction coil 17 is rectified by the diodes CR1 and CR2 to produce a d.c. output. This produces a positive voltage at the cathodes of the diodes CR1 and CR2 relative to the center tap of the induction coil 17. Charging current passes through the current sampling resistor R9 and through the diode CR5 to the tissue stimulator. The return current path is through the electrical lead 52 back to the center tap of the induction coil 17.

The telemetry circuit 12 is comprised in part of the transistors Q2 and Q3, which together form a free-running multivibrator coupled through capacitors C3 and C4. Bias current for transistors Q2 and Q3 comes from the collectors of transistors Q4 and Q5. The current to the bases of transistors Q2 and Q3 and capacitors C3 and C4 controls the frequency of the multivibrator. The collector current of Q4 and Q5 is controlled by the voltage drop across the series combination of the emitter resistors R4 and R5 and the emitterbase junction of transistors Q4 and Q5. The voltage across the emitter resistors R4 and R5 is almost equal to the voltage across the current sampling resistor R9 because the baseemitter voltage drops of transisotrs Q4 and Q5 are each close to the base emitter voltage drop of transistor Q6. A small amount of current is permitted to flow through transistor Q6 by its collector resistor R7 in order to permit a base-emitter voltage drop in transistor Q6 that will vary with temperature in the same way as do the base emitter voltage drops in transistors Q4 and Q5. Thus as the voltage across current sampling resistor R9 increases, a proportional voltage increase will occur across resistors R4 and R5. Since the collector current through transistors Q4 and Q5 is determined by the voltage across R4 and R5, the current through resistor R9 controls the frequency of the multivibrator in an almost linear fashion. The current flow from the collector of transistor Q2 is used to turn on and off the transistor Q1 at the frequency of the multivibrator. Every time Q1 is turned on, alternate sides of induction coil 18 are shorted for the separate halves of each cycle of the 21 kilohertz charging signal when it is present. Thus, when Q1 is turned on, the 21 kilohertz field is loaded down by the equivalent of a shorted coil equal to one side of inductor 18. The 21 kilohertz field from the power source 13 is thereby alternately loaded and unloaded at a rate determined by the free-running multivibrator. Connection of the transistor Q1 to the induction coil 18 is completed through the diodes CR3 and CR4, with the transistor Q1 acting as a switch to alternately vary the load of the charging field.

Figure 9:
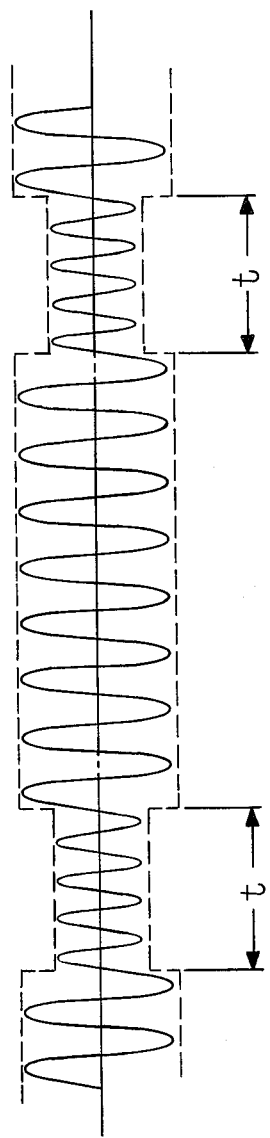
FIG. 9 illustrates the variation of the magnetic charging field with respect to time.

Magnetic field strength between the induction coils of the power source and charging circuit is illustrated with respect to time in FIG. 9. The interval $t$ during which loading of the charging field is increased (and field strength thereby reduced) varies with the frequency of operation of the telemetry circuit. As has previously been explained, the telemetry frequency is controlled by the transistors Q2 and Q3, which are in turn controlled by the current through the current sampling resistor R9. As the charging field energy increases, the initial current through resistor R9 is the charging current to the battery 15 of the tissue stimulator, since the shunt current regulator is not initially turned on. The shunt current regulator is comprised of the current shunting transistor Q7 and the shunt resistor R8, which biases the base of transistor Q7. The shunt current regulator maintains a constant current through the resistor R8, which is connected in series with the rectified output leads 51 and 52. The zener diode VR1, prevents the rectified output voltage on the leads 51 and 52 from becoming too great if battery 15 should open. This prevents dangerously high stimulation rates from developing in case of an open in that part of the tissue stimulator which is in series with battery 15 and thereby obviates the possibility of damage to the tissue being stimulated from excessive rates.

As the current through resistor R8 increases in the operation of the shunt current regulator, the voltage differential at the base emitter junction of transistor Q7 will also increase, which will cause transistor Q7 to conduct to a greater extent and thus to divert some of the current which is passing through the resistor. When Q7 starts to conduct, it tends to keep the current through resistor R8 relatively constant. If transistor Q7 is maintained at a constant temperature, resistor R8 can be selected for regulation at a predetermined current. For example, if one wanted to maintain a charging current of 40 milliamperes into the battery 15, and the base-emitter voltage drop required to initiate conductance in transistor Q7 is 0.4 volts, one would select a resistance value for resistor R8 such that 40 milliamperes would produce a 0.4 voltage differential between the base-emitter leads of transistor Q7. If the current began to increase beyond 40 milliamperes, transistor Q7 would conduct to an increasingly greater extent. Such an increasing load would alter the telemetry signal created by the transistor Q1. As long as the current through resistor R9 remains at 40 milliamperes or above, charging of the battery 15 is considered to be proper. The diode CR5 prevents any type of short from developing between leads 51 and 52 in the region between inductors 17 and 18 and diode CR5.

As a further safety feature, the implantable charging circuit of FIG. 2 utilizes a zener diode VR1 set at a predetermined maximum operating voltage and connected across the rectified output leads 51 and 52. This maximum operating voltage would typically not exceed five volts, and more desirably would not exceed 3.6 volts. This feature provides a positive protection against high voltage ever existing across the leads 51 and 52, and so provides another measure of safety against an inordinately large stimulus rate from occurring at catheter 16, and thereby prevents the occurrence of such dangers as triggering ventricular fibrillation when the heart is the tissue stimulated, an occurrence which usually results in the death of the patient. As previously explained, the diode CR5 in series with one of the rectified output leads 51 or 52 from the charging circuit prevents the cell 15 from being drained due to a short in the charging circuit, such as might occur in the transistors Q6 or Q7 or the capacitor C1.

A separate telemetry induction coil 18 is utilized in addition to the induction coil 17 of the electrical charging power source for safety reasons, although both of the coils 17 and 18 may be considered as part of the induction coil of the implantable charging circuit. The separate coils 17 and 18 are used to prevent any trouble that develops in the telemetry portion of the circuit from inhibiting proper charging of the cell 15. That is, any short or open circuits that occur between the resistors R4 or R3 and induction coil 18 will not affect the recharging of the battery 15.

The manner of operation of the magnetic output signal from the telemetry circuit 12 to the transducer 14 may be explained as follows. The magnetic flux existing between the induction coils of the external electrical charging power source 13 and those of the implantable charging circuit 10 varies in intensity in a regular manner as illustrated in FIG. 9. The extent to which the magnetic field generated by the power source 13 is loaded determines the maximum amplitude of the magnetic field. That is, the greater the loading by the charging circuit (and telemetry circuit) the smaller will be the amplitude of the magnetic field. The frequency of the rapid loading and unloading that occurs will be in direct proportion to the current being drawn through the resistor R9. Since all current up to a maximum level will flow through the rectified output leads 51 and 52 to charge the battery 15, any current less than this maximum passing through resistor R9 is indicative of inadequate charging of the battery 15. It is the telemetry circuit 12 (previously described) which senses this condition and signals the condition back to the induction coil 21 by modulating the frequency of the amplitude peak fluctuation of the charging field. That is, with inadequate charging, the period $t$ of amplitude peak variation in FIG. 9 will be inordinately long. As the induction coils of the power source are moved closer to a proper charging relationship with respect to the induction coil of the implanted charging circuit, the period $t$ in FIG. 9 will decrease. That is, the frequency of magnetic field strength peak amplitude will increase when this frequency increases sufficiently to indicate that the maximum charging current across resistor R9 has been reached. The electrical control signal generated in transducer 14 by the magnetic output signal from the telemetry circuit 12 will produce changes in the regulation of the power source 13. These changes include altering the condition of the charging status indicating light emitting diodes 26 and 27, altering the activation condition of the buzzer 28, generating a signal on circuit 59 to alter the output of the current control means 60 and turning on the timing means 61 to actuate register 31 to indicate that proper charging of the tissue stimulating system is occurring.

The telemetry circuit and transducer depicted in the drawings operate by loading down an existing electromagnetic field with a telemetry circuit, and governing operation of the power source 13 in accordance with the effect that the telemetry circuit 12 has on the electromagnetic field induced by the power source 13. It should be realized, however, that there are other forms of magnetic output signal generation and other forms of transducers appropriate for the different types of magnetic output signals. For example, (1) an electromagnetic signal could be transmitted back to a transducer at a frequency different from the charging frequency, (2) the power source could be turned off and on, and a short signal indicative of the previous charging current through resistor R9 could be returned to a transducer during the off period, or (3) a pietzoelectric crystal could be used in the telemetry circuit to generate an acoustic output signal indicating the degree of charge.

In addition, different parameters can be used as significant variables in the magnetic output signal. A signal frequency modulation linearly related to parameters such as charging current might be employed. Two different frequencies might be used to indicate adequate or inadequate charging. A variation of this latter mode of operation would be for the telemetry signal to be returned only if the unit were charging properly. In addition, various combinations of amplitude and frequency modulation could be employed in lieu of the form of frequency modulation utilized in the apparatus depicted.

Figure 4:
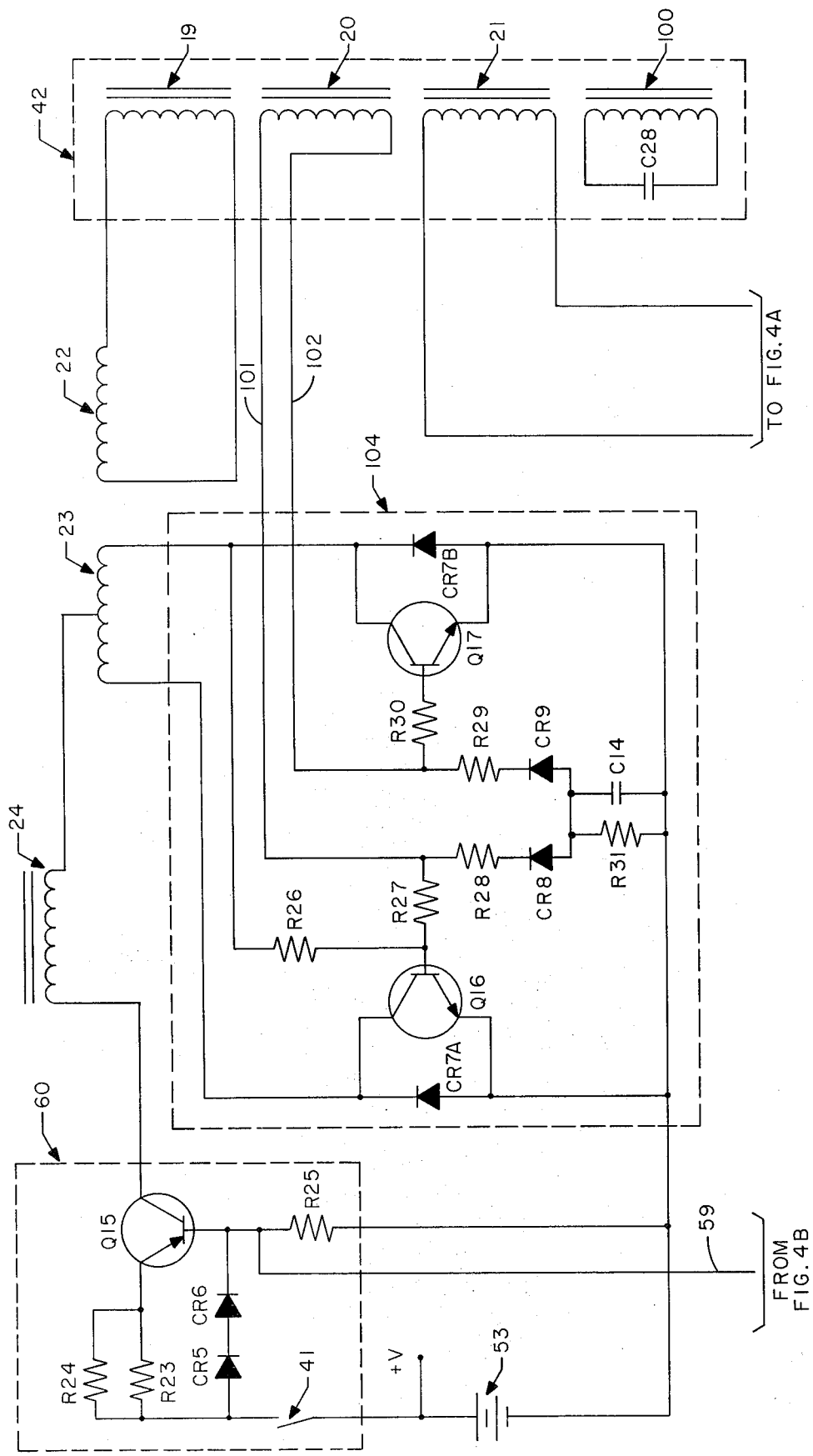
Figure 4A:
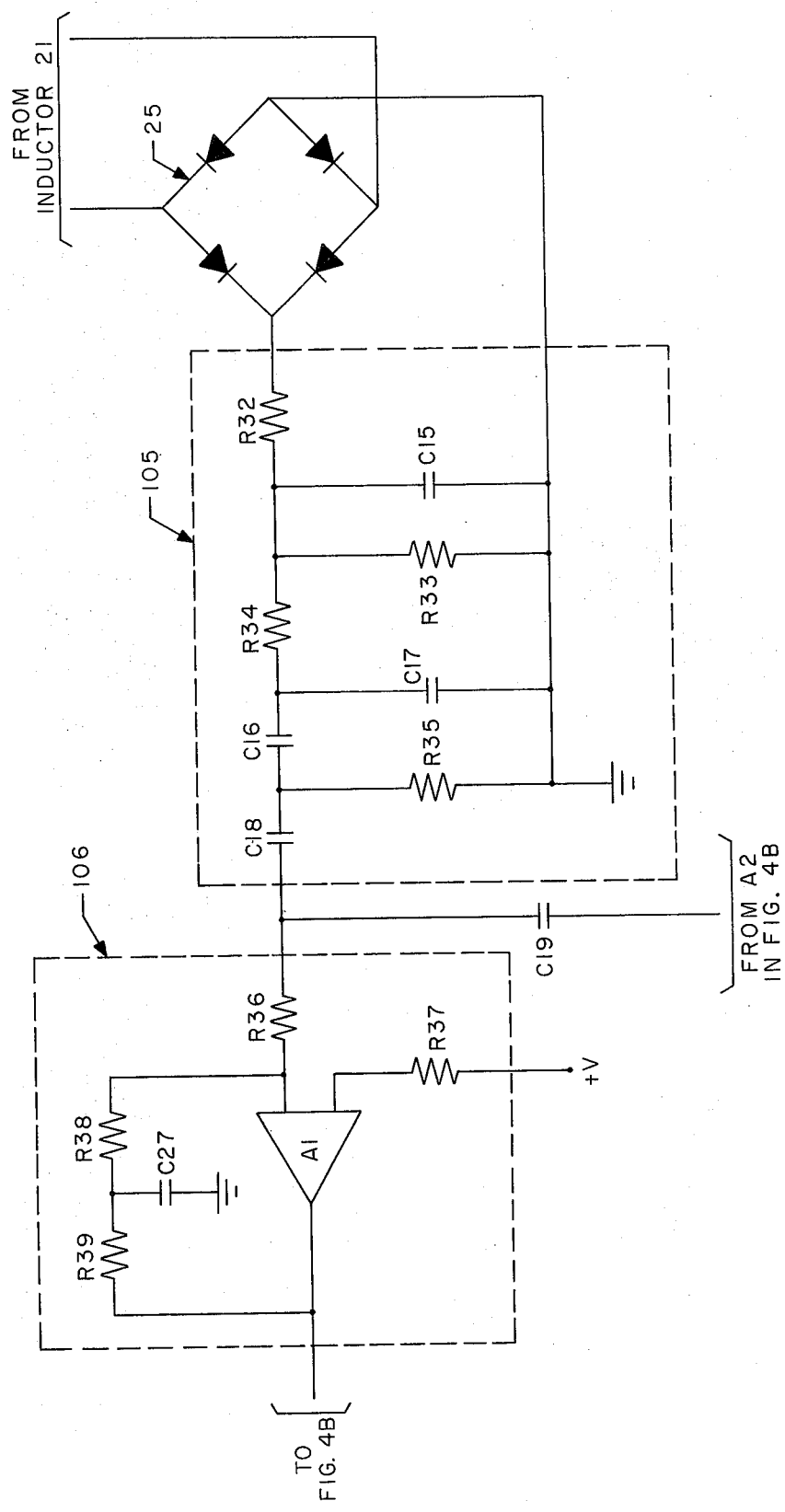
Figure 4B:
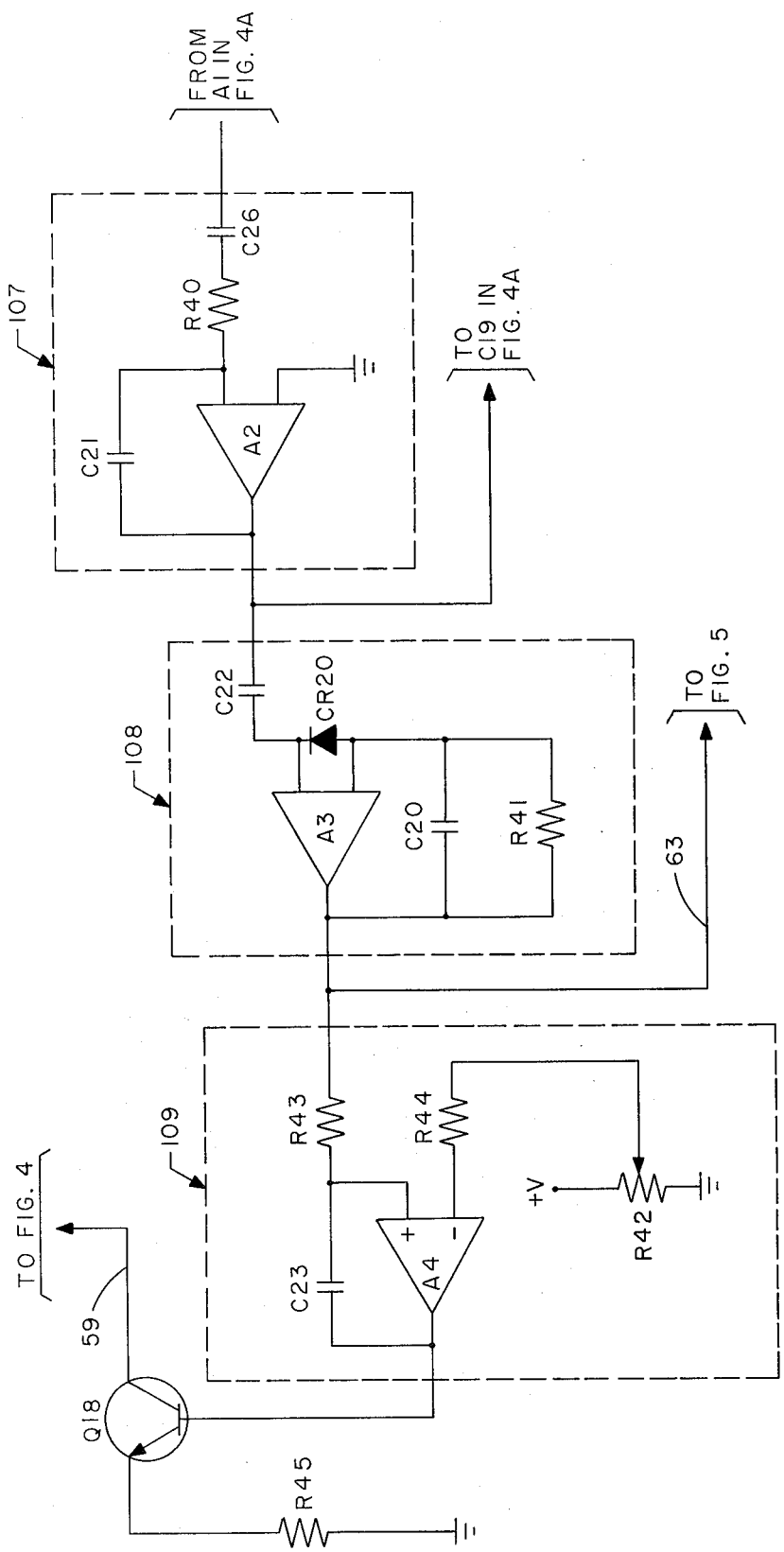

Returning to the power source illustrated in FIG. 4, a current control means 60 produces a constant current flow at its output into the induction coil 24. The current control means 60 includes resistors R23 and R24 connected in parallel with each other and in series with the base-emitter junction of transistor Q15, this combination being in parallel with diodes CR5 and CR6 located between the base-emitter junction of transistor Q15. A d.c. power source in the form of a rechargeable battery 53 has one terminal connected to these circuit elements and another terminal connected to the resistor R25, leading from the base of transistor Q15. Of course the electrical conrol signal on lead 59 from the transducer adjusts the current output from the current control means 60 to the induction coil 24 in order to adjust the strength of the magnetic field applied to the implanted charging circuit. That is, when the current passing through resistor R9 in the charging circuit exceeds a maximum operating level, the signal from circuit 59 will lower the output current from current control means 60. This lowered output current, through the use of induction coils 22, 23 and 24, results in a reduced magnetic field strength acting between the induction coils 19, 20 and 21 of the power source and induction coils 17 and 18 of the charging circuit.

The power oscillator circuit 104 consists of two transistors Q16 and Q17 that are directly connected to transformers 20 and 23 and inductively coupled to coils 19, 21 and 100. When the power oscillator circuit is first turned on, the base of transistor Q16 is made positive by resistor R26 which is connected to the primary of the transformer 23. The center tap of transformer 23 is connected to rechargeable battery 53 through the inductor 24 and through the current control means 60. When the base of transistor Q16 is made positive, Q16 conducts heavily and current flows through the half of primary 23 that is connected to the collector of transistor Q16. This current flow is transformer coupled to the secondary 22 and connected from there to the coil 19 on the charging head. Current flow in coil 19 magnetically induces a current flow in coil 20 in such a manner as to drive the base of transistor Q16 negatively and the base of transistor Q17 positively. This then causes transistor Q16 to turn off and transistor Q17 to turn on causing a new current to flow in the other half of primary 23. The current flow in the second half of coil 23 magnetically induces an opposite current to flow in coil 22. This current flowing now in the direction of coil 19 causes a reversal of the current flow in coil 20, which reverses the situation causing transistor Q16 to conduct and transistor Q17 to turn off. In this way oscillation is maintained. The frequency of the oscillator is controlled by the build-up and collapse of the magnetic field on the charging head 42 and the main controlling element for this build-up and collapse of the charging field is coil 100 and the capacitor C28, which is connected to it. Resistors R27 and R30 limit the current flowing into the bases of transistors Q16 and Q17. The circuit consisting of resistors R28, R29, and R31, and diodes CR8 and CR9, and capacitor C14 also protects the bases of transistors Q16 and Q17 from going positive too far. Diodes CR7A and CR7B prevent the bases of transistors Q16 and Q17 from being driven below the forward bias drop thereof and thus protects the collector-emitter junctions of transistora Q16 and Q17 from being damaged by excessive reverse biasing.

When lead 101 of coil 20 is positive relative to lead 102, the following current flow occurs: diode CR9 conducts and diode CR8 opens and the current flows through resistor R27 through the emitter-base junction of transistor Q16, (turning on transistor Q16) through the parallel network of resistor R31 and capacitor C14 through diode CR9 through resistor R29 back to lead 102. In that situation the baseemitter junction of transistor Q17 is back biased. When transistor Q16 starts to conduct, diode CR7B prevents the collector of transistor Q17 from going much more negative than the emitter of transistor Q17. Likewise, when lead 102 of coil 20 is positive relative to lead 101, the current flow is through resistor R30, through the emitter-base junction of transistor Q17 (which is turned on), through the parallel network of resistor R31 and capacitor C14 through diode CR8 (diode CR9 being reversed biased) through resistor R28 back to lead 101. CR7A prevents negative transients on the collector of transistor Q16 from damaging that transistor. When power is first applied to the circuit, transistor Q16 is immediately turned on through the bias current that flows through resistor R26. This guarantees that the circuit will start oscillating immediatley and not ever reach a state where neither transistor Q16 nor transistor Q17 conducts.

In the operation of the telemetry detection circuit, the signal of the magnetic field is picked up by coil 21 in the charging head 42, rectified by the full wave rectifying network 25 and is sent through the bank pass filter 105 consisting of resistors R32 through R35 and capacitors C15 through C18.

The output of the band pass filter 105 drives the tuned amplifier 106 consisting of amplifier A1, resistors R36 through R39 and capacitor C27. The tuned amplifier 106 is capacitively coupled via C26 to the low pass filter 107, consisting of amplifier A2, capacitor C21 and resistor R40. The output of the low pass filter is sent back through capacitor C19 to the tuned amplifier to stabilize that part of the circuit and is capacitively coupled through C22 to the frequency to voltage converter 108, consisting of amplifier A3, capacitor C20, resistor R41 and diode CR20. Diode CR20 develops a d.c. bias at the input of amplifier A3 which increases due to the reduction of the feedback signal caused by the reactance changes of capacitors C22 and C20 as a function of frequency. The output of the frequency to voltage converter 108 drives the comparator circuit 109 consisting of amplifier A4, resistors R42 through R44, and capacitor C23. By setting the value of resistor R42, the output of amplifier A4 goes positive when the output of amplifier A3 goes below the voltage to which the center tap of resistor R42 is adjusted. When this occurs, the output of amplifier A4 goes positive thereby turning on transistor Q18 which increases the base-emitter current in transistor Q18. The output of the voltage comparator amplifier A4 increases in the negative direction as the input frequency increases.

Increasing the current flow through transistor Q18 increases the current flow in transistor Q15 through line 59. Transistor Q15 is a constant current regulator.

The current flowing out of the collector of Q15 is determined by the voltage drop across the series diode circuit consisting of diodes CR5 and CR6 and the impedance of the parallel circuit consisting of resistors R24 and R23 which is in series with the base-emitter junction of transistor Q15. Increased current flow in line 59 causes the voltage across diodes CR5 and CR6 to increase thus increasing the current which the current regulator 60 will pass. Likewise, decreasing the current flow in line 59 decreases the current which the current regulator 60 will pass. It is through the line 59 that the transducer 14 acts upon the current control means 60 to adjust the strength of the magnetic field applied to the charging circuit 10.

Figure 5:
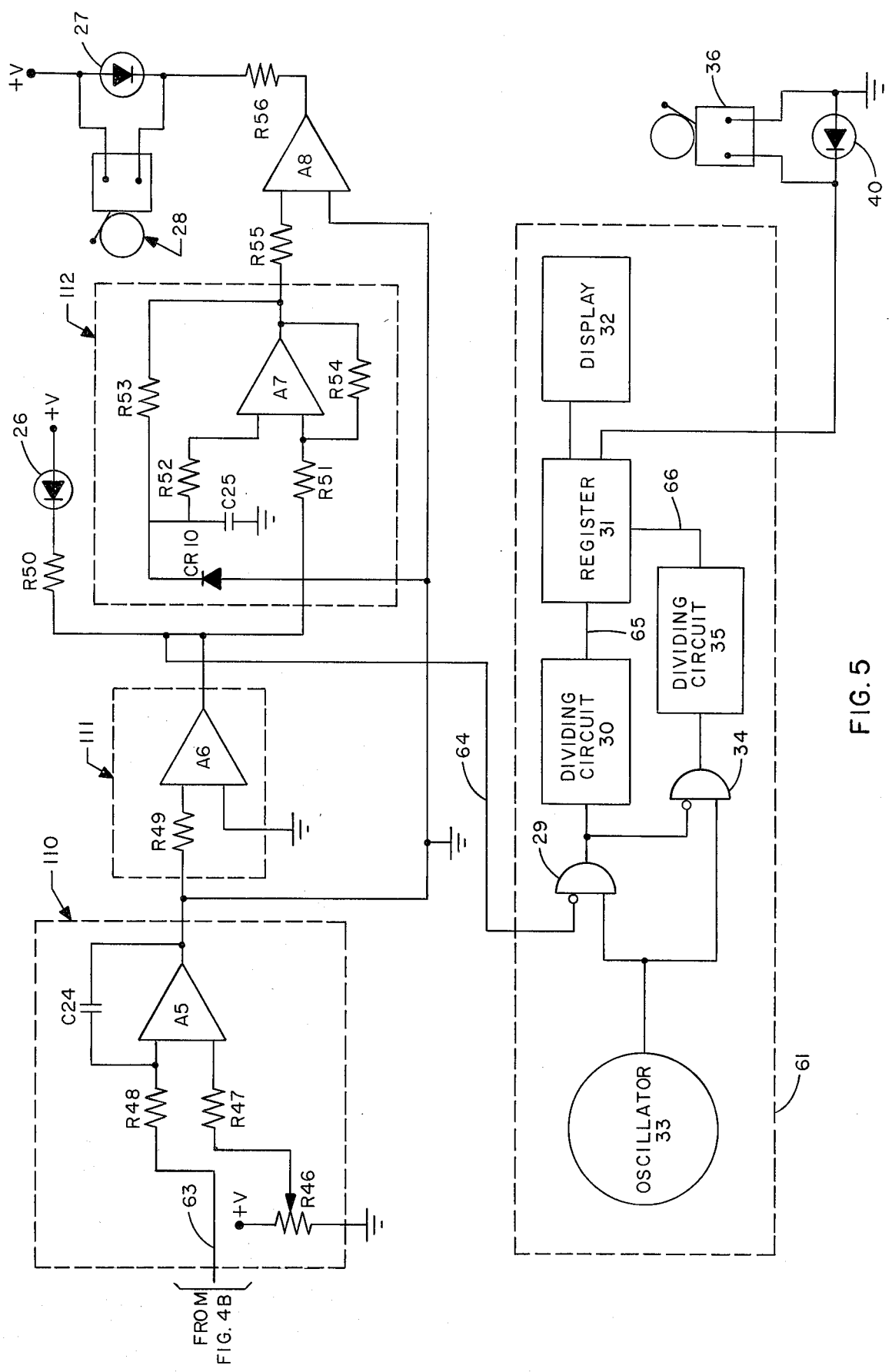
Figure 6:
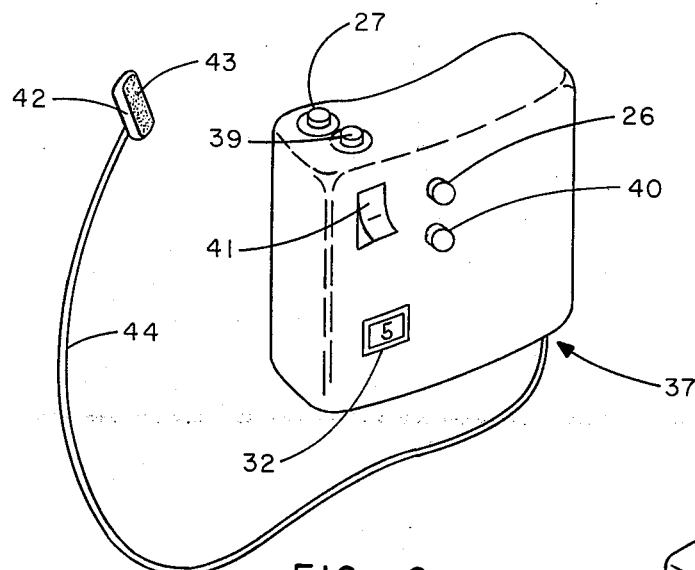

The frequency to voltage conversion system 108 also provides an output on lead 63. This output is connected to a comparison circuit 110 formed by the operational amplifier A5, resistors R46, R47 and R48, and capacitor C24, connected as indicated. The resistor R46 is adjustable to correspond to the appropriate operating charging voltage differential across the leads 51 and 52 of the charging circuit implanted in the patient. A lamp driver circuit 111 employing a resistor R49 and lamp driver amplifier A6, grounded as indicated, is connected through resistor R50 to a light emitting diode 26. This light emitting diode 26 provides a visual output display as indicated in FIG. 6 when the signal on circuit 63 is sufficiently great. The actuation of light emitting diode 26 indicates that the operating voltage has been achieved across the leads 51 and 52 in the charging circuit, and that the battery 15 is charging properly. Alternatively, if the signal on circuit 63 is insufficient to actuate light emitting diode 26, a signal is passed to a lamp and buzzer oscillator and driver circuit 112 employing an operational amplifier A7, resistors R51 through R54, diode CR10, and grounded capacitor C25, all connected as indicated in FIG. 5. The square wave output of circuit 112 is passed through a resistor R55 and amplified by lamp driver amplifier A8. A light emitting diode 27 is actuated by the square wave from amplifier A8 after it passes through the resistor R56. A buzzer is connected in parallel with light emitting diode 27.

The operator of the charging system is thereby appraised that the cell 15 is not being properly charged by the flashing yellow light from the light emitting diode 27 and by the intermittent buzzer 28. This is an indication to him to adjust the position of the charging head 42 containing the induction coils 19, 20 and 21 to more properly align these induction coils with the induction coils 17 and 18 of the charging circuit 10. Once proper alignment has been achieved, the yellow light 27 and the buzzer 28 will be rendered inactive and the green light 26 will be continuously lighted as long as the charging head 42 remains in place and at least the operating current is maintained through the resistor R9. It should be noted, that when a current larger than the operating current exists through the resistor R9, proper charging will continue to occur because the shunt current regulator (transistor Q7 and resistor R8) and the zener diode VR1 will prevent excessive current or voltage from being applied to the battery 15. In this event, a current control signal on line 59 will act to reduce the intensity of the magnetic field, and thereby reduce the current flowing through the resistor R9. None of this will affect the charging of the battery 15, however, unless the current flowing through resistor R9 drops below its operating level. This will be sensed by the transducer circuit 14 which will deactivate the green light emitting diode 26 and activate the intermittent operation of the buzzer 28 and yellow light emitting diode 27.

A further desirable feature of this invention is a timing means 61 responsive to the magnetic output signal and including a register 31 for storing a signal indicative of time elapsed during which the magnetic output signal indicates that the charging current is at least as great as a predetermined minimum operating level. That is, the timing means will store signals in the register 31 as long as the current through resistor R9 does not drop below its designed operating level. The timing means may employ a separate transducer for converting the magnetic output signal to an electrical signal, but preferably employs the transducer 14 heretofore described for that purpose. Similarly, the comparator employing the amplifier A5 and a driver employing amplifier A6 are also shared with other portions of the system. The comparator is employed as part of the timing means for providing a timing signal when actuated by a magnetic output signal exceeding a predetermined minimum level. A time recorder is provided in the form of an oscillator 33 supplying clock pulses to AND-GATE 29. In the presence of a timing signal on lead 64 (when lead 64 is low), the time recorder produces an output signal to actuate the register 31 for recording the time elapsed during which a timing signal is received by the timing means 61. In the embodiment illustrated, the timing means 61 further includes a dividing circuit 30 connected to the register 31 which operates to tabulate a number of identical charging periods of uniform duration in the register 31. Furthermore, the register 31 is incremented and decremented through the incrementing and decrementing leads 66 and 65 respectively. An increment from lead 66 derived from the oscillator 33 signifies a time interval of discharge of the battery 15 in its normal performance within the body of the patient. Each such time interval of discharge will require an offsetting predetermined charging interval to restore the electrical charge dissipated thereby from the cell 15. In this connection it is necessary that a dividing circuit 35 be chosen so that the incrementing and decrementing signals on the leads 66 and 65 respectively maintain the appropriate relationship in the register 31 to accurately correlate charging time periods with corresponding discharging intervals. In the circuit illustrated, the time recorder, formed by the oscillator 33 and the AND-GATE 29, is connected through the dividing circuit 30 to the decrementing lead 65. A clock mechanism, formed by the oscillator 33 and the AND-GATE 34, is connected through the dividing circuit 35 to the incrementing lead 66. Since the output of AND-GATE 29 is connected to the inverted input of AND-GATE 34, it can be seen that the existence of a timing signal (low voltage) on lead 64 inhibits an output from the clock mechanism to the incrementing lead 66.

Preferably, the register 31 is provided with upper and lower limits which inhibit the register from decrementing to a number less than zero and which also inhibit the register from incrementing to a number greater than a predetermined maximum allowable number. This is achieved through conventional inhibiting circuitry. If either of these events occur, an alarm 36 is sounded. Otherwise, the number currently recorded in register 31 may be visually ascertained from the display unit 32.

As an added feature, the buzzer 36 may be briefly actuated by the register 31 using conventional circuitry each time a charging period is recorded therein. In this manner, a patient is automatically provided with an audio signal which informs him that he need charge his cardiac pacing unit no more at that particular time.

Figure 7:
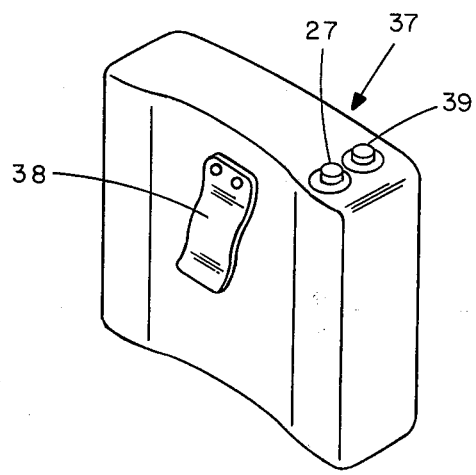
FIG. 7 is a rear perspective view of the power source and transducer of FIG. 6.

One physical embodiment of a power source for a rechargeable cardiac pacing system constructed according to this invention is illustrated in FIGS. 6 and 7. The power source 37 utilizes its own rechargeable battery 53 which is connected to an induction coil located in the charging head 42 by means of an electrical cord 44. The unit is turned on and off by means of a switch 41. Improper charging is signalled by the intermittent flashing of a yellow light 27 and by the intermittent sound of the buzzer 28 enclosed within the casing of the power source 37. The green light 26 indicates proper charging while a blue light 40, connected in parallel with the buzzer 36, indicates the expiration of a predetermined interval of proper charging, as recorded in the register 31. The unit 37 may be fastened to the belt of the patient by means of hook 38. A signal indicated by a red light 39 signifies that the charge of the rechargeable battery 53 in the portable power source is at a voltage level less than a predetermined minimum allowable voltage level. The patient knows that he therefore must recharge the rechargeable battery 53 as soon as possible.

Figure 8:
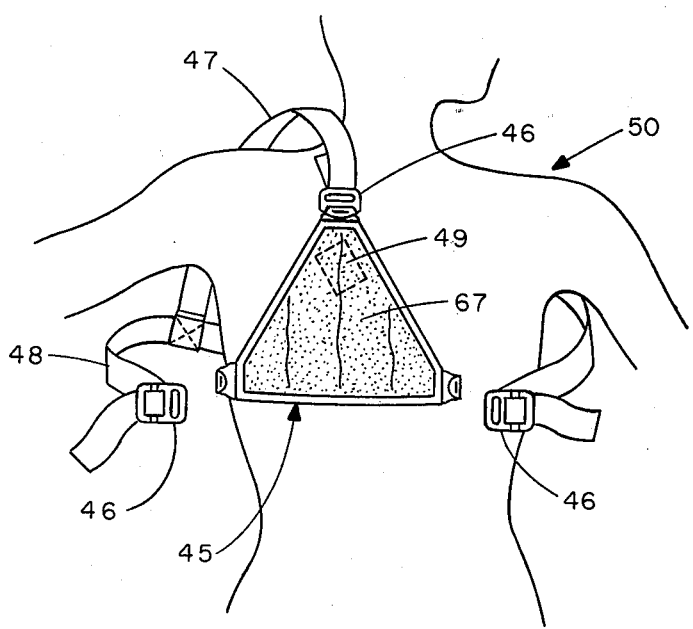
FIG. 8 illustrates the character of the special vest of this invention.

To facilitate the proper alignment of the induction coils in the charging head 42 of the power source with the induction coils in the charging unit 10, a vest 45 is provided for fastening in position about the upper portion of a human torso indicated generally at 50. Vest 45 is provided with straps 47 and 48 and clasps 46. The vest 45 also has a contact surface 67 for positioning proximate to the skin area of the patient in the vicinity of the charging circuit 10. The charging head 42 is also equipped with a contact surface 43. One of the contact surfaces 43 and 67 includes a multiplicity of flexible hooks projecting outward from the contact surface. The other of the contact surfaces includes a loop pile projecting outward therefrom. This form of fastening means is illustrated in U.S. Pat. No. 3,009,235. The contact surface 43 is positionable in face-to-face relationship with respect to the contact surface 67 whereby the hooks from the one contact surface become engaged in the pile of the other contact surface with only a slight contact between the two surfaces. The contact surfaces, when positioned in this face-to-face relationship, thereby resist lateral displacement and angular rotation with respect to each other from forces acting laterally therebetween. That is, once the contact surface 43 is in the position indicated at 49 in FIG. 8, where proper charging of the charging circuit 10 is achieved, the weight of the charging head 42 or any shifting of the patient's torso 50 will not cause misalignment between the induction coils.

Figure 3:
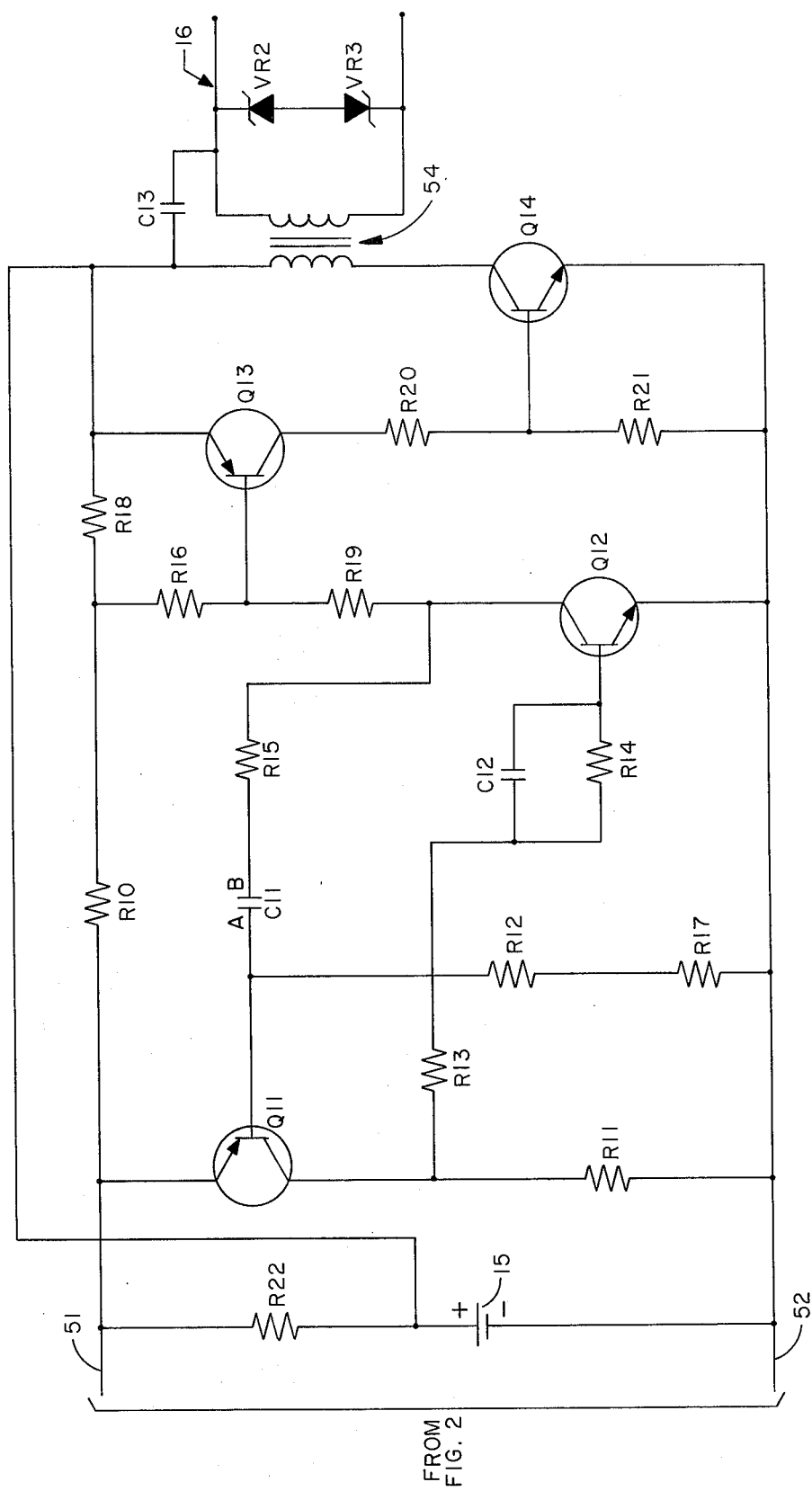

The circuit design of the tissue stimulator in FIG. 3 is that of a fixed rate pacer. The improvement of this invention is equally applicable to demand pacers as well. The physical packaging of the charging circuit, telemetry circuit, and tissue stimulator are largely described in U.S. patent application Ser. No. 267,114, filed on June 28, 1972, now abandoned in favor of continuation-in-part application Ser. No. 464,441, filed Apr. 26, 1974. Briefly stated, however, the pulse generating circuitry employed comprises a transistor network including transistors Q11, Q12, Q13, and Q14 powered by the rechargeable battery 15 which is charged by current from leads 51 and 52 through resistor R22 from the charging circuit. Transistors Q11, Q12, resistors R10 through R19, the base emitter junction of Q13 and capacitors C11 and C12 comprise a relaxation oscillator that produces a train of current pulses through the collector of Q12. The period between the pulses is determined by the time to charge C11 via terminal A through high resistance resistors R12 and R17 towards the negative voltage at the negative terminal of battery 15, while the B terminal of capacitor C11 is being held relatively constant at the positive voltage of battery 15 through the series connection of low resistance resistors R15, R19, R16, R10 and R22 (R16 is shunted partially by the base emitter junction of Q13 and R18). This is mainly determined by the time constant of C11 and the combined value of R12 and R17. During the time between pulses, O11 and O12 are both non-conducting. However, when the base of Q11 becomes negative to the emitter of Q11 by an amount sufficient to cause current to flow in the collector of Q11, current from the collector of Q11 will start to flow through R13 and charging C12 through the base emitter junction of Q12 thus turning on Q12. Current from the collector of Q12 will, in turn, flow through R15 reverse charging C11 through the base emitter junction of Q11. Thus Q11 is turned on even harder. This regenerative action causes Q11 and Q12 to turn on suddenly. Q11 and Q12 stay on until C11 is charged up to the point when the charging current through the base of Q11 is not sufficient to maintain the regenerative feedback. This is determined by time constants R15, C11 and R14, R13, C12.

The battery charging current from line 51 through R22 causes an increase in the rate of the relaxation oscillator by increasing the effective voltage powering the oscillator by the voltage drop across R20, R21 and R22. Q13 and Q14 form a power amplifier to drive a pulse of current through the primary of transformer 54. Zener diodes VR2 and VR3 form a protection circuit across the leads from the secondary coil of the transformer 54. The resistor R18 is of some significance in that in conjunction with Zener diode VR1 it serves to prevent dangerously high frequencies from developing in the fixed rate circuit illustrated in FIG. 3 if battery 15 were to open circuit and a charging current applied. It should be kept in mind that a demand pacer circuit might well be employed in place of the fixed rate pacer circuitry of FIG. 3.

Figure 10:
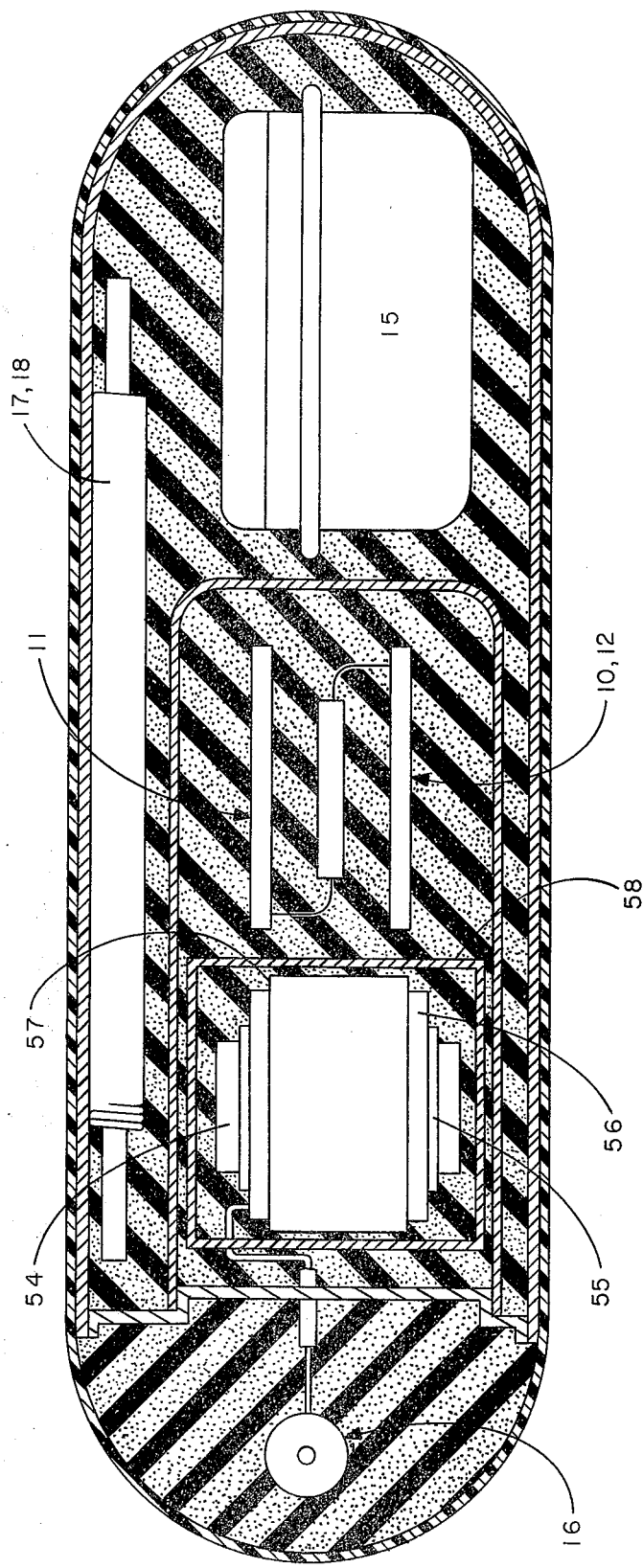
FIG. 10 illustrates the structural configuration of the implanted portions of the tissue stimulating system of FIG. 1.

The physical configuration of the pacer component is as illustrated in FIG. 10. The considerations of placement and the materials used are largely described in U.S. patent application Ser. No. 267,114, filed on June 28, 1972 and now abanoned. One very significant difference should be noted, however. An annular electrically conductive band 57 encircles the transformer 54 of the tissue stimulating circuit. The band 57 is positioned in insulated concentric arrangement with respect to the primary coils 55 and the secondary coils 56 of the transformer 54. A highly conductive closed container 58 encapsulates electrically conductive band 57 and the transformer 54. Container 58 is electrically insulated from band 57 and the transformer 12 as illustrated. The purpose of utilizing the metal band 57 and the container 58 is to prevent the charging field from the power source 13 from causing current flow in the transformer 54. Once subjected to a charging field, a current flow is induced in the metal band 57 and container 58. This current flow in band 57 and container 58 induces an opposing magnetic field that cancels the effects of the original magnetic field from the power source 13 or charging circuit 10. The transformer 54 is thereby rendered insensitive to the fields from charging head 42 and charging circuit 10. The metal band 57 is preferably constructed of copper while the metal box 58 is usually constructed of a magnetically shielding metal such as soft iron.

The foregoing embodiment depicts the invention in the form deemed most preferable. Other modifications and alterations will be apparent to those familiar with cardiac pacer and other tissue stimulating devices.

I claim:

1. A rechargeable tissue stimulating system comprising:
    means for implantation in the body of a living subject for applying electrical pulses to stimulate living tissue in order to maintain bodily functions of said subject, said means including a rechargeable DC voltage source supplying the power for said pulses;
    internal charging means for implantation beneath the skin of said subject and connected to said source for providing a charging current to said voltage source, said internal charging means including a first induction coil;
    an external means for supplying power by induction to said internal charging means and including a second induction coil for setting up a magnetic field and for positioning external to a living subject and proximate to said first induction coil;
    telemetry means connected to said internal charging means for detecting the magnitude of said charging current received by said DC voltage source and providing a magnetic output signal to said external power source indicative of the magnitude of said charging current; and
    transducer means forming a part of said external means for supplying power for converting said magnetic output signal to an electrical signal, and including current control means responsive to said electrical signal for adjusting the strength of the magnetic field applied to said internal charging means in response to changes in said electrical signal, such that the magnitude of said charging current is maintained within predetermined limits.

2. The tissue stimulating system of Claim 1 in which said first induction coil includes first and second output leads, and wherein said internal charging means further comprises first and second diodes respectively in series with said first and second output leads to rectify the output of said first induction coil,
    a current sampling resistor means connected in series to one of said diodes on the side opposite said first coil, and
    a shunt current regulator connected between the other of said diodes on the side opposite said first coil, and to said current sampling resistor on the side opposite said one diode, said regulator including a current shunting transistor with the collector thereof in series with said current sampling resistor, the emitter thereof connecting with said other diode, said regulator also including a shunt resistor biasing the base of said transistor and connected across the emitter and base thereof.

3. The tissue stimulating system of claim 2, wherein the implantable charging circuit further comprises a third diode in series with either of said first and second diodes, to prevent said internal charging means from draining current from said DC voltage source in the event of a short in said internal charging means.

4. A rechargeable cardiac pacing system for maintaining stimulating pulses to the heart of a patient comprising:
    means for positioning beneath the skin of a patient for applying stimulating pulses to the heart of the patients, including a rechargeable DC voltage source, and catheter means, said catheter means including electrodes connected to said pulse generating circuits;
    means for internal positioning beneath the skin of a patient for recharging said DC voltage source and including a first induction coil;
    an external means for supplying power by induction to said internal recharging means, said external means including a second induction coil for external positioning with respect to the patient proximate to the first induction coil;
    telemetry means connected to said internal recharging means for detecting the magnitude of a charging current received by said DC voltage source, and for providing a magnetic output signal indicative thereof;
    timing means responsive to said magnetic output signal and including means for storing a signal indicative of time elapsed during which the magnetic output signal indicates that the charging current is at least as great as a predetermined minimum operating level.

5. The cardiac pacing system of claim 4 wherein said means for storing comprises a register and said timing means further includes transducer means for converting said magnetic output signal to an electrical signal, a comparator for providing a timing signal when actuated by a magnetic output signal exceeding a predetermined minimum level, and time recorder means connected to actuate said register for recording time elapsed during which a timing signal is received thereby.

6. The cardiac pacing system of claim 5 wherein said timing means further includes a dividing means connected to said register operative to tabulate a number of identical charging periods of uniform duration in said register.

7. The cardiac pacing unit of claim 6 wherein said register is further provided with means for generating an audio output each time a charging period is recorded in said register.

8. The cardiac pacing system of claim 4 wherein said register decrements as well as increments and includes inputs corresponding thereto, with said time recorder means being connected to said decrementing input, and wherein said timing means further comprises clock means connected to said incrementing input, whereby said register counts the discharged time intervals during which said rechargeable DC source discharges during its normal use, as well as the charging time intervals during which said DC source receives said timing signal indicative of proper charging, said register offsetting said discharge and charge intervals against each other to indicate the remaining recommended recharging time needed to fully restore said DC source.

9. The cardiac pacing system of claim 8 in which said time recording means includes an oscillator and a first AND gate in which said oscillator is in series with one input of said gate, the second input of said gate receiving said timing signal, and in which said timing means also includes said oscillator as well as a second AND gate, with said oscillator being in series with one input of said second gate, and the output of said first gate being connected to the other input of said second gate, as well as in series with said decrementing register input, and the output of said second gate being in series with said incrementing input, whereby the occurrence of one of said timing signals inhibits the output of said clock means.

10. The cardiac pacing unit of claim 8 wherein said register includes means for furnishing a limit signal either upon the occurrence of a predetermined maximum increment, or upon the occurrence of a decrement to zero, and in which said timing means further includes limit alarm means connected to said register and responsive to said limit signal to warn of an unacceptable charge or discharge state.

11. The cardiac pacing system of claim 4 further including means for generating an audio signal actuated by operation of said means for supplying power and connected to said telemetry means, said audio signal generating means further including means for disabling said audio output in response to a magnetic output signal indicative of a charging current at least as great as a predetermined minimum operating level.

* * * * *

UNITED STATES PATENT OFFICE
CERTIFICATE OF CORRECTION

Patent No. 3,942,535   Dated March 9, 1976

Inventor(s) Joseph H. Schulman

It is certified that error appears in the above-identified patent and that said Letters Patent are hereby corrected as shown below:

The Assignee is Pacesetter Systems, Inc.,
of Sylmar, California

Signed and Sealed this

Twenty-eighth Day of December 1976

[SEAL]

Attest:

RUTH C. MASON
*Attesting Officer*

C. MARSHALL DANN
*Commissioner of Patents and Trademarks*